US00PP32613P2

(12) United States Plant Patent
Hansen

(10) Patent No.: US PP32,613 P2
(45) Date of Patent: Dec. 8, 2020

(54) ***PENSTEMON* PLANT NAMED 'ONYX AND PEARLS'**

(50) Latin Name: *Penstemon digitalis*
Varietal Denomination: Onyx and Pearls

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/873,025

(22) Filed: Jan. 15, 2020

(51) Int. Cl.
*A01H 5/02* (2018.01)
*A01H 6/68* (2018.01)

(52) U.S. Cl.
USPC ..... Plt./465

(58) Field of Classification Search
USPC ..... Plt./465
CPC ... A01H 5/02; A01H 5/00; A01H 5/12; A01H 6/68
See application file for complete search history.

(56) References Cited

U.S. PATENT DOCUMENTS

PP30,569 P2 * 6/2019 Korlipara ..... A01H 5/02 Plt./465

OTHER PUBLICATIONS

Friends of the UC Davis Arboretum & Public Garden 2019, retrieved on Jul. 20, 2020, retrieved from the Internet at https://arboretum.ucdavis.edu/sites/g/files/dgvnsk1546/files/inline-files/Final_Web_INV_9_28_19_0.pdf, pp. 1,23. (Year: 2019).*

* cited by examiner

*Primary Examiner* — June Hwu

(57) ABSTRACT

The new and distinct cultivar of ornamental, winter-hardy, beardtongue plant, *Penstemon* 'Onyx and Pearls' with strictly upright, tightly-compact strong stems, numerous pale-purple to near-white flowers for about four weeks contrasting with dark purple foliage that retains its coloration through the season. Useful in the landscape as a specimen plant, en masse or container plant, and attractive to hummingbirds.

2 Drawing Sheets

Botanical classification: *Penstemon digitalis*.
Variety denomination: 'Onyx and Pearls'.

STATEMENT REGARDING PRIOR DISCLOSURES UNDER 37 CFR 1.77(b)(6)

The first non-enabling disclosure of the claimed plant, in the form of a photograph and brief description on a website operated by Walters Gardens, Inc. was on Feb. 1, 2019. Subsequently, on May 29, 2019 Walters Gardens, Inc. advertised the new plant in the "Walters Gardens 19-20 Catalog" followed by the first sale on Jul. 8, 2019. Walters Gardens, Inc. obtained the plant and all information relating thereto, from the inventor. No plants of *Penstemon* 'Onyx and Pearls' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct plant of beardtongue, botanically known as *Penstemon* 'Onyx and Pearls' and will be referred to hereinafter also by its cultivar name 'Onyx and Pearls' and as the new plant. The new plant cultivar of beardtongue is a hardy herbaceous perennial grown for landscape use.

*Penstemon* 'Onyx and Pearls' is a seed selection derived from second generation selfed *Penstemon* 'Pocahontas' U.S.

Plant Pat. No. 24,804 collected by the inventor in the fall of 2013 at a wholesale perennial nursery in Zeeland, Mich. All subsequent evaluations were performed in a full-sun trial garden at the same nursery with loamy sand soil and irrigation and fertilizer as required. The single seedling plant was assigned the breeder code 13-39-2 while being selected for further trials during the summer of 2015. The new plant was propagated by basal shoot cuttings at the same nursery in Zeeland, Mich., and the original plant and the cuttings evaluated over the next two years until final approval for introduction in the summer of 2015. The resultant asexually propagated cuttings have been stable and identical to the original plant in successive asexual propagations.

SUMMARY OF THE INVENTION

*Penstemon* 'Onyx and Pearls' differs from its parent as well as all other hardy beardtongue known to the inventor in a combination of traits. The following characteristics in combination distinguish 'Onyx and Pearls' from all other beardtongue plants known to the inventor:

1. Strictly upright growth with tightly-compact strong stems;
2. Foliage developing and maintaining dark purple coloration in high light intensity;
3. Flowering with numerous pale-purple to near-white flowers for four weeks beginning early summer in Michigan.

The nearest comparison cultivars are *Penstemon* 'Blackbeard' U.S. Plant Pat. No. 30,052, 'Midnight Masquerade' U.S. Plant Pat. No. 29,603, 'Pocahontas' U.S. Plant Pat. No. 24,804, 'TNPENDB' U.S. Plant Pat. No. 30,569 and 'Dark Towers' U.S. Plant Pat. No. 20,013. The new plant is taller to slightly taller than all the above listed cultivars, with larger and more rounded apices of basal foliage and more numerous flowers that are a lighter colored than all of the above. A more complete comparison is provided in Table 1.

TABLE 1

| Cultivar | Color | Corolla length | Flowering height |
|---|---|---|---|
| 'Blackbeard' | light purple | 27 mm | 80 cm |
| 'Dark Towers' | light purple | 34 mm | 75 cm |
| 'Midnight Masquerade' | strong purple | 23 mm | 78 cm |
| 'TNPENDB' | strong purple | 30 mm | 55 cm |
| 'Pocahontas' | strong purple | 25 mm | 95 cm |
| 'Onyx and Pearls' | very pale purple | 33 mm | 102 cm |

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color. The plant used in the photograph is a three-year-old plant grown in full sun field in loamy sand soil in trial gardens of a nursery in Zeeland, Mich.

DETAILED BOTANICAL DESCRIPTION

Figure 1:
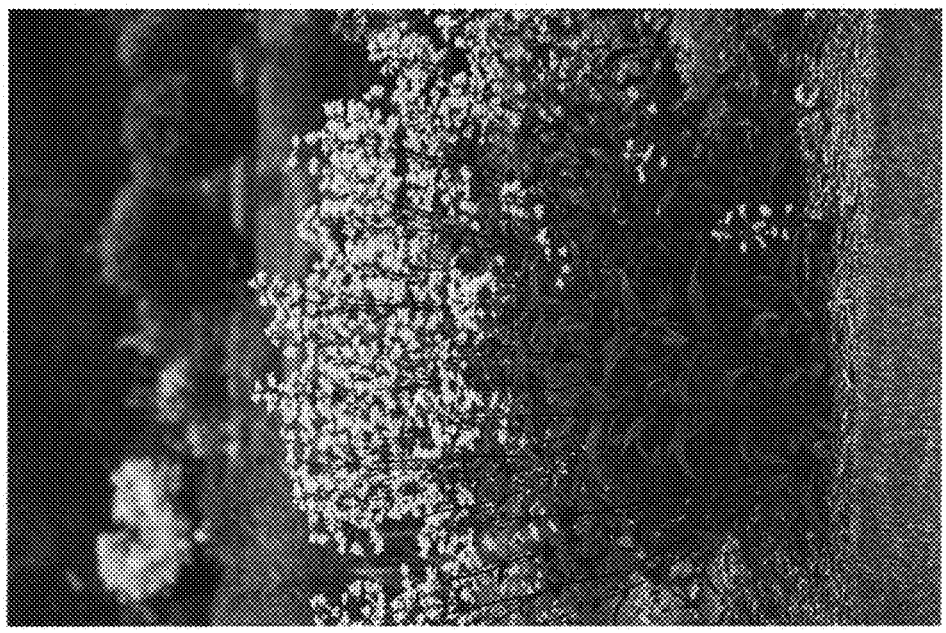
FIG. 1 shows the new plant in the landscape in peak flower with very dark foliage.
Figure 2:
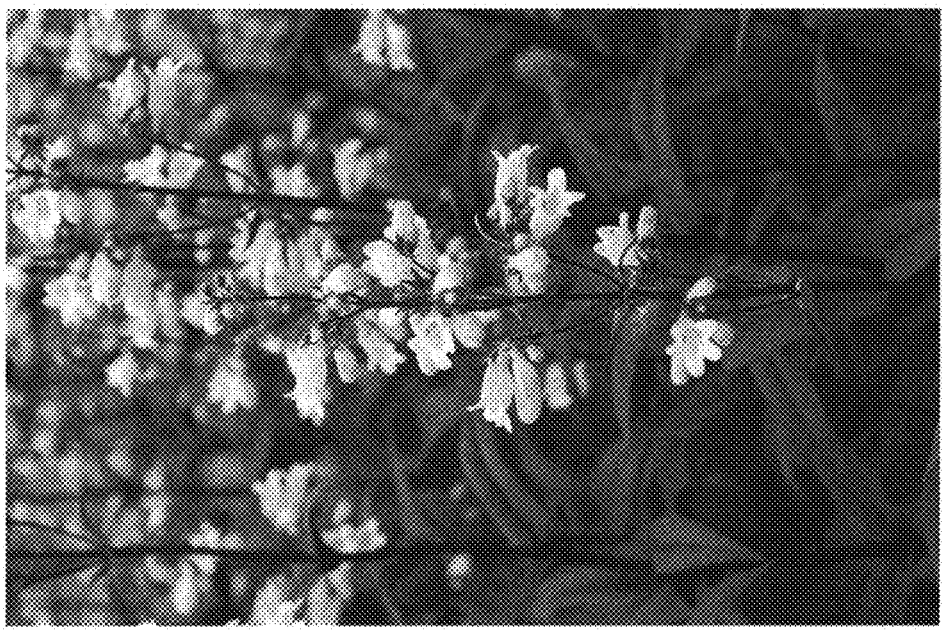
FIG. 2 shows a close-up of the flowers and buds.
Figure 3:
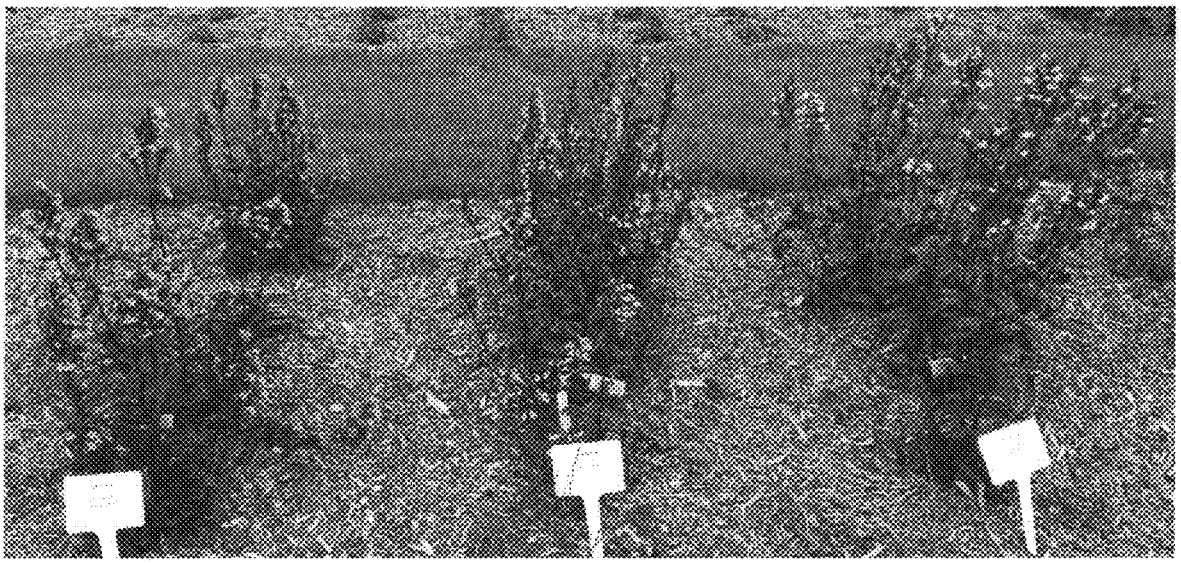
FIG. 3 shows a comparison of two-year-old plants with 'Midnight Masquerade' on the left, 'Blackbeard' in the center, and 'Onyx and Pearls' on the right.

The following is a detailed description of *Penstemon* 'Onyx and Pearls' as observed and compared to other cultivars for two years in trial gardens and production fields at a nursery in Zeeland, Mich. The following description is of a three-year-old plant growing in a full-sun display garden in Zeeland, Mich. with limited supplemental fertilizer and irrigation as needed and without any pinching or plant growth regulators. The new plant has not been observed under all possible environments, and the phenotype may vary slightly with different environmental conditions, such as temperature, light, fertility, moisture and maturity levels, but without any change in the genotype. The color descriptions are in accordance with the 2015 edition of The R.H.S. Colour Chart of The Royal Horticultural Society, London, England, except where common dictionary color terms are used.

Parentage: The female (seed) parent is a selection of selfed 'Pocahontas' and the male (pollen) parent was the same selection of selfed 'Pocahontas';

Plant habit: Herbaceous winter-hardy, perennial with upright rigid stems emerging from the base in the spring; up to about 36 stems per plant; flowering in branched panicle;

Plant size: About 102.0 cm in height, average stem 96.0 cm tall, and about 65.0 cm in width about 60 cm above soil;

Root description: Fibrous, well-branched, developing to thickness of about 1.0 mm; color between RHS 161A and RHS 161B;

Propagation: Shoot-tip cuttings; root initiation occurs in about 14 days at a temperature of 22° C.;

Growth rate: Moderately vigorous;

Crop time: About 12 to 14 weeks to finish in a 4 liter pot from rooted plug;

Stem description: Terete; oppositely branched in distal region; glabrous; lustrous; average about 62.0 cm long below flowers and about 8.0 mm across near base;

Stem color: Variable between RHS 187A and RHS N187A;

Internode: Average about 10 per stem, average internode length about 6.2 cm, larger toward flowers;

Internode color: Same as surrounding stem;

Foliage description: Simple; glabrous adaxial and abaxial; basal leaves—in rosette, oblanceolate to ovate, decumbent, acute apex, sessile with attenuate base to petiolate, margin serrulate; cauline leaves—opposite, lanceolate, narrowly acute apex, with sessile, truncate, clasping base; margin serrate, teeth more pronounced on cauline leaves than basal leaves; abaxial and adaxial surface glabrous, slightly lustrous adaxial and matte abaxial; fragrance not detected;

Leaf size: Basal leaves to about 22.0 cm long and about 6.0 cm wide; cauline leaves to about 17.5 cm long and about 5.0 mm wide; size decreasing distally; average size about 13.5 cm long and about 4.0 cm wide;

Leaf color: Young expanding adaxial nearest RHS 187A, abaxial blend between RHS N186C and RHS 187A; mature adaxial nearest RHS 187A with slight undertone of nearest 137A, abaxial blotchy nearest RHS 137B with blush of nearest RHS N187C;

Leaf venation: Pinnate;

Petiole: On basal leaves only; attenuate with clasping base; glabrous; to 7.5 cm long and 12.0 mm wide at base;

Petiole color: Adaxial margins nearest RHS 137A, midrib nearest RHS 145D distally and heavily blushed to solid RHS 187C; abaxial margins nearest RHS 146C, midrib nearest blend between RHS 145D and RHS 193A distally and proximally nearest RHS 187C;

Vein color: Young abaxial midrib nearest RHS 158C with slight blush of nearest RHS 70B in basal 1.0 cm then distal one-third to one-half RHS 187C, young abaxial secondary veins RHS 187C; young adaxial midrib nearest RHS N186D, secondary veins nearest RHS 187C; mature abaxial and adaxial midrib and secondary veins nearest RHS 187A;

Inflorescence: Panicle; to about 34.0 cm long and about 15.0 cm across; with up to 170 closely arranged flowers per inflorescence and 4,000 per plant;

Pedicel: Cylindrical; glabrous, lustrous; size variable, about 5.0 to 11.0 mm long and 1.0 mm diameter;

Pedicel color: Nearest RHS 187A;

Peduncle: Branched panicle with up to ten branches; smooth, glabrous; main stems vertical, branches at about 20 degrees below vertical; to about 102 cm tall and 8.0 mm diameter base;

Peduncle color: Nearest RHS 187A;

Flower buds about one day prior to opening: About 27.0 mm long and about 10.0 mm wide; oblong ovoid to clavate; rounded apex; basal 8.0 mm of corolla tube narrowed to about 3.0 mm diameter, with rounded base;

Bud color: Apical 2 to 3 mm nearest RHS 11D, remainder nearest RHS NN155B with veins of nearest RHS N80B;

Flowering season: Beginning in early June and flowering for about five weeks;

Flowers: Zygomorphic; perfect; bilabiate with upper and lower lip gamopetalous in about basal 25.0 mm; about 33.0 mm long and about 27.0 mm across and 24.0 mm tall; face opening to nearly flat; lasting about five to seven days;

Flower attitude: Mostly outward;

Flower fragrance: None detected;

Corolla: Bilabitate; ventral petal with three lobes; dorsal petal with two lobes; glandular abaxial, glabrous adaxial ventral petal and pubescent on adaxial dorsal petal; dorsal petal lobes about 7.0 mm long and 6.0 mm across at fusion with rounded apices; two ventral petals side lobes about 8.0 mm long and about 7.0 mm across at fusion, center ventral lobe about 8.0 mm long and 7.0 mm across; all lobes with rounded apices; tube base about 8.0 mm long and 3.0 mm diameter at base; throat about 17.0 mm long and face about 10.0 mm diameter, fused in basal 25.0 mm; lobes with rounded apex and entire margin;

Corolla color: Adaxial basal 8.0 mm nearest RHS NN155C, throat and distal lobes nearest RHS NN155B with veins in throat of more white than RHS N82D, lobes of first day opened flowers lightly blushed with nearest RHS 84D and lightening in older flowers to nearest RHS NN155C to RHS NN155D; abaxial basal 2.0 mm nearest RHS 152D, next distal 6.0 mm of abaxial tube blend between RHS N82D and RHS 84D, throat portion nearest RHS 84D dorsally and ventrally between RHS 84D and RHS NN155D, abaxial lobes lighter than blend between RHS 84D and RHS NN155D;

Gynoecium: One pistil; about 27.0 mm long;

*Style*.—Straight; cylindrical; glabrous; about 22.0 mm long and about 0.5 mm diameter; color nearest RHS NN155B.

*Stigma*.—Oblong, about 0.5 mm wide and about 0.7 mm long; color nearest RHS 155D.

*Ovary*.—Ovoid; with rounded base and acute apex; about 5.0 mm long and 3.0 mm across; color nearest a blend between RHS 139A and RHS 137A.

Androecium: Four; didynamous; slightly arcuate;

*Filaments*.—About 23.0 mm long and about 0.8 mm in diameter; color nearest RHS 153D in basal 2.0 mm, distally nearest RHS NN155C.

*Anther*.—Elliptic; dorsifixed; longitudinal; about 3.0 mm long and 2.0 mm across, versatile; color nearest RHS 202A dorsally and nearest RHS 155D ventrally.

*Staminode*.—Single; straight; cylindrical; about 15.0 mm long and 0.5 mm diameter; bearded pubescence to about 2.5 mm long on distal half of dorsal side.

*Staminode color*.—Nearest NN155C; bearded pubescence variable with both RHS 161A and RHS 155D.

*Pollen*.—Abundant; color nearest RHS 155D.

Calyx: Stellate; campanulate; fused in basal 3.0 mm; not adpressed to corolla; about 8.0 mm long and about 10.0 mm across;

Sepals: Five; lanceolate; narrowly acute apex and fused base; entire margin; to about 1.5 mm wide above fusion point and 8.0 mm long; glandular to puberulent abaxial and adaxial;

Sepal color: Abaxial color abaxial and adaxial nearest RHS 187A;

Fruit: Septicidal capsule; ovoid with acute apex and rounded base; about 10.0 mm long and 5.0 mm across; color as developing nearest RHS 187A and with maturity nearest RHS 177A; effective as colorful cut flower;

Seed: Irregular; flattened, dried; about 1.0 mm long and about 1.0 mm diameter; color between RHS 200A and RHS 202A;

*Hardiness to at least U.S.D.A. zones* 4 *to* 9.—The new plant performs best with good drainage and is resistant to drought once established.

*Pest and disease resistance*.—Resistance beyond that typical of beardtongue plants has not been observed. No other susceptibility or resistance to diseases or pests has been observed except that which is common to *Penstemon*.

It is claimed:

1. A new and distinct cultivar of hardy beardtongue plant, *Penstemon* 'Onyx and Pearls' as herein described and illustrated.

* * * * *